United States Patent [19]

Komatsubara et al.

[11] Patent Number: 5,525,580
[45] Date of Patent: Jun. 11, 1996

[54] SUBSTITUTED BENZOYL CYCLIC ENONE, PROCESS FOR PREPARATION, AND HERBICIDE

[75] Inventors: Kenichi Komatsubara, Tsukuba; Tadashi Sato, Kawasaki; Kenji Mikami; Yuji Yamada, both of Tsukuba, all of Japan

[73] Assignee: SDS Biotech K.K., Tokyo, Japan

[21] Appl. No.: 182,895

[22] Filed: Jan. 14, 1994

[30] Foreign Application Priority Data

Mar. 18, 1993 [JP] Japan .................... 5-084063

[51] Int. Cl.$^6$ .................................... A01N 37/10
[52] U.S. Cl. .................... 504/348; 504/349; 504/350; 568/9; 568/11; 568/12; 568/15; 568/17; 568/29; 568/30; 568/31; 568/42; 568/43; 568/300; 568/322
[58] Field of Search ............... 568/31, 63, 327, 568/29, 30, 42, 43, 306, 326, 15, 17, 10; 504/349, 350, 348; 560/9, 11, 12

[56] References Cited

U.S. PATENT DOCUMENTS

| | | | |
|---|---|---|---|
| 4,762,551 | 8/1988 | Knudsen | 71/103 |
| 4,837,352 | 6/1982 | Knudsen | 558/396 |
| 4,854,966 | 8/1989 | Knudsen | 71/103 |
| 4,869,748 | 9/1989 | Knudsen | 71/123 |
| 4,918,236 | 4/1990 | Knudsen et al. | 568/306 |
| 4,957,540 | 9/1990 | Knudsen et al. | 71/123 |
| 4,995,902 | 2/1991 | Brunner | 71/94 |
| 5,006,158 | 4/1991 | Carter et al. | 71/98 |
| 5,089,046 | 2/1992 | Lee et al. | 71/103 |

FOREIGN PATENT DOCUMENTS

| | | | |
|---|---|---|---|
| 338992 | 10/1989 | European Pat. Off. | C07C 79/36 |
| 5408 | 1/1991 | Japan | A01N 41/10 |
| 120202 | 5/1991 | Japan | A01N 43/16 |
| 120203 | 5/1991 | Japan | A01N 43/90 |

*Primary Examiner*—James H. Reamer
*Attorney, Agent, or Firm*—Allen E. Norris

[57] ABSTRACT

Compounds represented by general formula (I), herbicides or selective herbicides for paddy field containing said compounds as active ingredients, method of controlling growth of undesirable plants by applying the herbicides on places where control is desired.

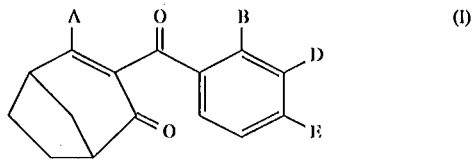

wherein A represents a —S(O)nR$^1$ in which n is 0 or 2 and R$^1$ represents a (substituted) lower alkyl; a cycloalkyl; a (substituted) benzyl; a (substituted) phenyl; or a —OR$^2$ in which R$^2$ represents a (substituted) phenyl;
B represents a halogen, a nitro, a lower alkyl, or a lower alkylsulfonyl;
D represents a hydrogen, a lower alkyl, a lower alkoxy, a lower alkoxymethyl, or a lower alkoxycarbonyl;
E represents a halogen, a (substituted) lower alkoxy, a lower alkylthio, a (substituted) lower alkylsulfonyl, or a lower alkylsulfonyloxy.

The herbicides of the present invention can prevent a wide variety of noxious weeds and further selectively prevent weeds on paddy field with considerably reduced phytotoxicities on rice plant.

10 Claims, No Drawings

SUBSTITUTED BENZOYL CYCLIC ENONE, PROCESS FOR PREPARATION, AND HERBICIDE

BACKGROUND OF THE INVENTION

1. Field of the Invention

The present invention relates to novel substituted benzoyl cyclic enone derivatives, a process for preparing the same, herbicidal compositions containing the same as active ingredients, and a method for controlling the growth of plants using such herbicidal compositions.

2. Description of Related Art

As prior arts, 2-substituted benzoyl-1,3 -cyclohexanedione compounds are known as having certain herbicidal activities as disclosed in U.S. Pat. No. 5,006,158.

U.S. Pat. No. 4,762,551 discloses some compounds including 3-(substituted thio)-2-benzoylcyclohex-2-enones, and EP 338,992 discloses substituted aryl bicyclodiones as herbicidal active compounds. However, the compounds of the present invention differ from those compounds as disclosed in the prior arts in their chemical structures and combination of substituents thereon, and are never found in any other prior art references, thus the compounds of the present invention are found to be novel. Further, the above-described known compounds are recognised to be highly toxic on rice plants and hence they have been difficult to be used as paddy field herbicides for rice.

SUMMARY OF THE INVENTION

The compounds of the present invention represented by general formula (I) below exhibit herbicidal activities on a wide variety of weeds with low phytotoxicity to rice, and due to optimal soil mobility and water solubility, they are recognised as more practical herbicides which are acceptable to the world in terms of environmental protection as compared with other dione type compounds disclosed in the prior art references.

For example, after adding the chemical to surface water of paddy field, and then leaving it for 3 days in a condition under which water is drained as a rate of 3 cm in depth per day (i.e., the total amount of water drained during 3 days is 9 cm in depth), movement of the compounds shown in Table 3 were found to be 1 to 5 cm in depth of the soil in contrast to the known herbicidal active dione compounds disclosed in U.S. Pat. No. 5,006,158, U.S. Pat. No. 4,762,551 and EP 338,992 which exhibited soil mobility of 6 to 9 cm in depth.

Also, many of the compounds of the present invention have such excellent characteristics as having small water solubilities by from about one several tenth to about one several ten thousands as compared with the above-described known herbicidally active dione compounds.

The present invention provides novel compounds represented by general formula (I)

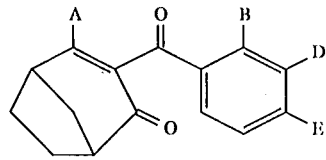

wherein A represents a —S(O)nR$^1$ group in which n is 0 or 2 and R$^1$ represents a lower alkyl group having 1–4 carbon atoms which may be substituted with a lower alkoxycarbonyl group having 2–3 carbon atoms;

a cycloalkyl group having 3–6 carbon atoms;

a benzyl group which may be substituted with 1 to 3 of halogen atoms, methyl groups and/or nitro groups;

a phenyl group which may be substituted with 1 to 5 halogen atoms, 1 to 3 lower alkyl groups having 1–4 carbon atoms, a lower alkoxy groups having 1–4 carbon atoms, a halomethyl group, a nitro group, a cyano group and/or an amino group substituted with one or two alkyl or alkylsulfonyl groups having 1–2 carbon atoms; or a —OR$^2$ group in which R$^2$ represents a phenyl group which may be substituted with 1 to 5 halogen atoms and/or 1 to 3 lower alkyl groups having 1–3 carbon atoms;

B represents a halogen atom, a nitro group, a lower alkyl group having 1–2 carbon atoms, or a lower alkylsulfonyl group having 1–2 carbon atoms;

D represents a hydrogen atom, a lower alkyl group having 1–2 carbon atoms, a lower alkoxy group having 1–4 carbon atoms, a lower alkoxymethyl group having 2–4 carbon atoms, or a lower alkoxycarbonyl group having 2–5 carbon atoms;

E represents a halogen atom, a lower alkoxy group having 1–3 carbon atoms which may be substituted with 1 to 3 fluorine atoms, a lower alkylthio group having 1–3 carbon atoms, a lower alkylsulfonyl group having 1–3 carbon atoms which may be substituted with 1 to 3 fluorine atoms, or a lower alkylsulfonyloxy group having 1–3 carbon atoms.

Practical herbicides, particularly those which are useful for paddy rice being major agricultural crops in countries where rice is a staple food, must have various advantageous properties, for example, (1) high herbicidal activity, (2) wide weeds spectrum, (3) low phytotoxicity on objective plant (paddy rice plant), (4) moderate water solubility, moderate soil mobility, (5) low toxicity on fish and manmals, (6) moderate stability in soil and easy degradation in nature after certain periods of time, and the like.

Taking these properties into consideration, preferred compounds among those compounds represented by general formula (I) are those represented by general formula (II) below.

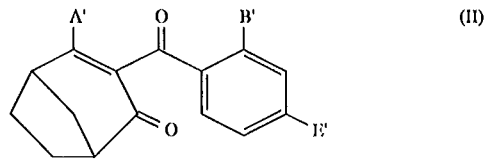

wherein

A' represents a group —S—(O)nR$^3$ in which n is 0 or 2 and R$^3$ represents a phenyl group which may be substituted with 1 to 5 halogen atoms or 1 to 3 lower alkyl groups having 1–4 carbon atoms, B' represents a halogen atom or a nitro group, and E' represents a halogen atom, or a lower alkylsulfonyl group having 1–3 carbon atoms which may be substituted with 1 to 3 fluorine atoms.

Specific examples of most preferred compounds include the following compounds:

(1) 3-(2-chloro-4-methylsulfonylbenzoyl)-4-phenylthiobicyclo[3.2.1]oct-3-en-2-one (Compound No. 95);

(2) 3-(2-chloro-4-methylsulfonylbenzoyl)-4-(4-methylphenylthio)-bicyclo[3.2.1]oct-3-en-2-one (Compound No. 97);

(3) 3-(2-chloro-4-methylsulfonylbenzoyl)-4-phenylsulfonylbicyclo[3.2.1]oct-3-en-2-one (Compound No. 108);

(4) 3-(2-chloro-4-methylsulfonylbenzoyl)-4-(2,6-dimethylphenylthio)-bicyclo[3.2.1]oct-3-en-2-one (Compound No. 79);

(5) 3-(2-chloro-4-methylsulfonylbenzoyl)-4-(3-chlorophenyltio)-bicyclo[3.2.1]oct-3-en-2-one (Compound No. 98); and (6) 3-(2-nitro-4-methylsulfonylbenzoyl)-4-(2,6-dichlorophenylthio)-bicyclo[3.2.1]oct-3-en-2-one (Compound No. 68).

The following Table 1 illustrates the excellent activities and properties of these most preferred compounds as mentioned above for paddy rice herbicides.

TABLE 1

| Compound No. | a | b | c | d |
|---|---|---|---|---|
| 95 | A | 1 cm | A | A |
| 97 | A | 1 cm | A | B |
| 108 | A | >5 cm | A | B/C |

TABLE 1-continued

| Compound No. | a | b | c | d |
|---|---|---|---|---|
| 79 | C | 1 cm | A | B |
| 98 | B | 1 cm | A | B |
| 68 | B | 1 cm | A | A | a: herbicidal activity to Barnyard grass in terms of $ED_{90}$ value against Barnyard grass
A: 32–64 gram a.i./ha
B: 64–125 gram a.i./ha
C: more than 125 gram a.i./ha
b: soil mobility
c: selectivity to rice in terms of the value of $ID_{10}$ Rice/$ED_{90}$ Barnyard grass.
A: >8
d: fish toxicity in terms of TLm (48) killifish
A: ≧10 ppm
B: 0.5–10 ppm
C: ≦0.5 ppm The compounds represented by general formula (I) can be prepared, for example, according to the following reaction scheme. In the sequence below, symbols have the same meanings as defined above, X represents a halogen atom.

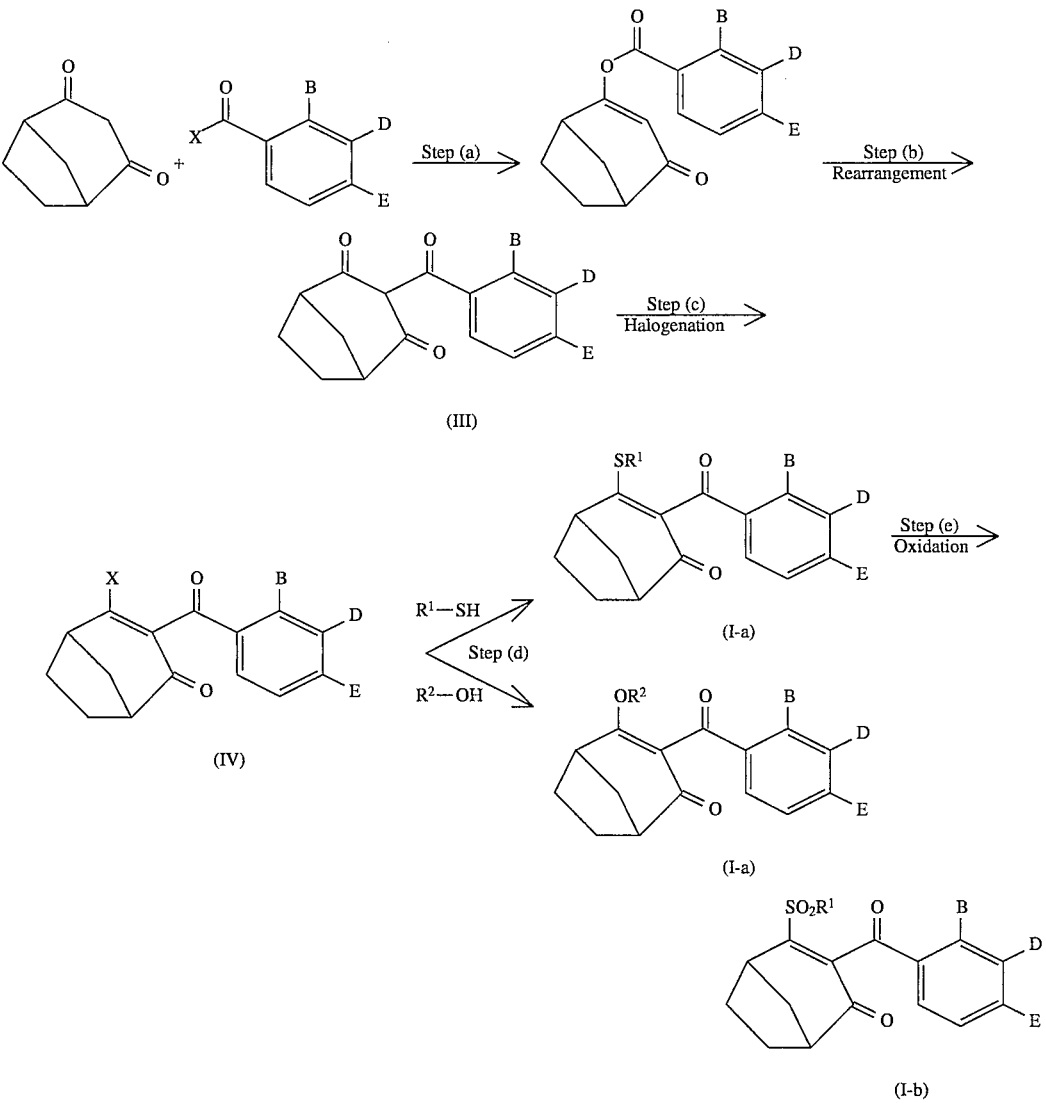

The reaction in Step (a) proceeds advantageously in a solvent which is inert under the reaction conditions, for example, dichloromethane, chloroform, tetrahydrofran, toluene, acetonitrile and the like, preferably in the presence of an organic base, for example, triethylamine. Suitable reaction temperature is within the range of from 0° to 40° C., e.g., 20° C.

The rearrangement reaction in Step (b) can be carried out in the presence of a catalyst, for example, 4-dimethylaminopyridine, a Lewis acid or cyanide donnor with moderate base.

Suitable Lewis acid catalyst used in the rearrangement reaction may be, for example, aluminum chloride, zinc chloride or tin (IV) chloride, and suitable cyanide donnor may be, for example, acetonecyanhydrin with triethylamine.

Examples of suitable solvent include dichloromethane acetonitrile or toluene.

Reaction temperature is preferably from 0° C. to reflux temperature, preferably room temperature (about 20° C.).

Table 2 shows specific examples of benzoyldione (III), intermediate compounds thus prepared.

TABLE 2-1

| Compound No. | B | D | E | Properties (mp. °C.) |
|---|---|---|---|---|
| 1 | NO$_2$ | H | Cl | 134 |
| 2 | NO$_2$ | H | Br | 142 |
| 3 | Cl | H | SO$_2$CH$_3$ | 156–158 |
| 4 | Cl | H | OSO$_2$CH$_3$ | |
| 5 | Cl | Cl | Cl | |
| 6 | Cl | Cl | SO$_2$CH$_3$ | |
| 7 | CH$_3$ | H | Br | 92–95 |
| 8 | NO$_2$ | H | SO$_2$CH$_3$ | 148 |
| 9 | NO$_2$ | OCH$_3$ | OSO$_2$CH$_3$ | |
| 10 | NO$_2$ | H | OSO$_2$CH$_3$ | 140 |
| 23 | NO$_2$ | H | SC$_2$H$_5$ | 75 |
| 24 | CH$_3$ | H | Cl | 94 |
| 30 | NO$_2$ | H | SCH$_3$ | 126 |
| 31 | NO$_2$ | OCH$_3$ | Cl | |
| 32 | NO$_2$ | OC$_2$H$_5$ | Cl | Oil |

TABLE 2-2

| Compound No. | B | D | E | Properties (mp. °C.) |
|---|---|---|---|---|
| 33 | Cl | CH$_3$ | Cl | |
| 34 | Cl | H | Cl | |
| 35 | NO$_2$ | H | SO$_2$CHF$_2$ | 147–150 |
| 36 | NO$_2$ | H | SO$_2$CHF$_2$ | Gum |
| 37 | NO$_2$ | H | Bu-t | Oil |
| 38 | SCH$_3$ | H | SCH$_3$ | |
| 44 | NO$_2$ | H | SPr-n | 117–119 |
| 45 | NO$_2$ | H | SBu-t | |
| 46 | Cl | H | SC$_2$H$_5$ | Oil |
| 47 | Cl | H | SO$_2$Pr-n | 101 |
| 48 | Cl | H | SCH$_3$ | 107–108 |
| 49 | Cl | H | SPr-n | Gum |
| 50 | NO$_2$ | H | SC$_2$H$_5$ | 77–78 |
| 51 | NO$_2$ | H | SPr-i | |
| 52 | NO$_2$ | H | SO$_2$Pr-n | |
| 53 | NO$_2$ | H | SO$_2$C$_2$F$_5$ | |
| 54 | NO$_2$ | H | SO$_2$CF$_2$—CHFCF$_3$ | |

Generally, in the halogenation reaction in Step (c), benzoyldione (III) is dissolved in an inert solvent such as chloroform, carbontetrachloride, dichloromethane, dichloroethane, tetrahydrofuran, dioxane, benzene, toluene, xylene and the like. Then, an excess amount (usually, 100 to 300 mol %) of thionyl halide or oxalyl halide (practically thionylchloride or oxalylchloride) is added, followed by addition of a catalytic amount of amine or amide, such as dimethylformamide or pyridine. The reaction mixture is stirred at a temperature of from room temperature to the boiling point of the solvent from 1 hour to 1 day, then the product can be isolated by a conventional method.

The products of Step (c) above represented by the formula (IV) are novel compounds and are easily converted in Step (d) to the compounds of the present invention of the formula (I).

In the reaction of Step (d), halide (IV) and thiol (R$^1$—SH) or phenol (R$^2$—OH) corresponding to the desired compound are dissolved, usually in an stoichiometric amount respectively, in an inert solvent such as tetrahydrofuran, chloroform, dichloromethane, toluene and the like, and then organic base such as triethyamine is added in an amount of 100–200 mol % of the starting materials.

The reaction is carried out at a temperature of from 0° C. to the boiling point of the solvent (preferrably at room temperature) for from 1 hour to 1 day, then the product can be isolted by a conventional method.

The oxidation reaction in Step (e) is carried out by a conventional method using an oxidating agent such as m-chloroperbenzoic acid after dissolving sulfide (I-a) in an inert solvent such as dichloromethane, chloroform or carbontetrachloride.

PREPARATION EXAMPLE

The followings are typical examples of preparation of the compounds of the present invention from the intermediate (III).

Preparation Example 1

3-(2-Chloro-4-methylsulfonylbenzoyl)bicyclo[3.2.1]-octane-2,4-dione (0.99 g) was dissolved in 15 ml of dichloromethane, and 0.8 ml of oxalyl chloride was added to the resulting solution. Further, a catalytic amount (1–2 drops) of dimethylformamide was added thereto, and the reaction mixture was stirred at room temperature for 30 minutes, followed by refluxing for 2 hours. After the solvent and excessive oxalyl chloride were distilled off under reduced pressure, the chloride thus obtained was dissolved in 20 ml of tetrahydrofuran without purification. The chloride was purified and identified separately. The analytical data is shown below;

mp. 154°–157° C., δ (CDCl$_3$) 7.7–8.0(3H,m), 3.05(3H,s) 2.8–3.4(2H,m), 1.6–2.3 (6H,m).

To the solution were added 0.386 g of 2,6-dimethylthiophenol and then 0.39 ml of triethylamine while ice cooling.

After it was stirred at room temperature for 3 to 4 hours, the reaction mixture was poured into water, and extracted with ethyl acetate. The organic layer was washed with 1N hydrochloric acid, and then with water, and dried over anhydrous sodium sulfate.

Crude crystals obtained by distilling off the solvent under reduced pressure was washed with diisopropyl ether to obtain 1.11 g of the objective compound (Compound No. 79 in Table 3). (Yield from dione: 83.7%)

Preparation Example 2

In 30 ml of tetrahydrofuran was dissolved 1.61 g of the chloride obtained in the same manner as in Preparation Example 1 above using 3-(2-nitro-4-methylsulfonylbenzoyl)bicyclo[3.2.1]octane-2,4-dione. The chloride as mentioned above was identified separtely. The analytical data is shown below;

mp. 120°–123° C., NMR (CDCl$_3$) δ 8.4(1H, d,J=2), 8.15(1H, dd,J=8.2), 7.6 (1H,d,J=8), 3.1(3H,s), 1.5–3.4(8H, m).

To the resulting solution were added 0.674 g of 4-chlorobenylmercaptan, and then 0.59 ml of triethylamine.

After being stirred at room temperature for one night, the reaction mixture was subjected to the same work-up as in Preparation Example 1 to obtain 1.6 g of the objective compound (Compound No. 63 in Table 3). (Yield: 73.2%)

Preparation Example 3

In 20 ml of dichloromethane was dissolved 0.8 g of Compound (63) obtained in Preparation Example 2, and 0.68 g of m-chloroperbenzoic acid was added portionwise to the resulting solution while ice cooling. The reaction mixture was stirred as it was for several hours. After completion of the reaction was confirmed by TLC (thin layer chromatography), the reaction mixture was diluted with about 50 ml of dichloromethane, and washed with an aqueous sodium hydrogen metasulfite solution and then with a 5% aqueous potassium carbonate solution, followed by drying over anhydrous sodium sulfate.

Crystals obtained by distilling off the solvent under reduced pressure was washed with diisopropyl ether to obtain 0.7 g of the objective compound (Compound No. 64 in Table 3). (Yield: 82.3%)

Preparation Example 4

Procedures of Preparation Example 2 were repeated except that there were used 1.92 g of 2-chloro-3-(2-nitro-4-methylsulfonylbenzoyl)bicyclo[3.2.1]oct-2-en-4-one obtained in the same manner as in Preparation Example 1, 0.9 g of 2,6-dichlorothiophenol, 0.7 ml of triethylamine, and 35 ml of tetrahydrofuran. Thus 1.85 g of the objective compound (Compound No. 68 in Table 3) was obtained (yield: 69.8%).

Preparation Example 5

Reaction procedures of Preparation Example 2 were repeated except that there were used 1.87 g of 2-chloro-3-(2-nitro-4-methylsulfonylbenzoyl)bicyclo[3.2.1]oct-2-en-4-one obtained in the same manner as in Preparation Example 1, 0.52 g of methyl thioglycolate, 0.68 ml of triethylamine, and 35 ml of tetrahydrofuran. Thereafter, the reaction mixture was subjected to silica gel chromatography (eluant: ethyl acetate/n-hexane: 1:4 to 1:1) to obtain 0.52 g of the objective compound (Compound No. 71 in Table 3) was obtained (yield: 23.4%).

Preparation Example 6

In 20 ml of tetrahydrofuran was dissolved 1.0 g of the chloride prepared in the same manner as in Preparation Example 1 from 1.0 g of 3-(2-nitro-4-methylsulfonylbenzoyl)bicyclo[3.2.1]octane-2,4-dione. Then, 0.58 g of 2,4,6-trichlorophenol and then 0.41 g of triethylamine was added to the resulting solution.

After being stirred at room temperature for one night, the reaction mixture was subjected to the same work-up as in Preparation Example 1, and crude extracts were crystallized from diethyl ether to obtain 0.5 g of the objective compound (Compound No. 113 in Table 4). (Yield: 32.7%)

Preparation Example 7

3-(2-chloro-4-methylsulfonylbenzoyl)-bicyclo[3.2.1.]octane-2,4-dione (1.0g) was dissoloved in 10 ml of dichloromethane, and 0.3 ml of thionylchloride was added to the resulting solution. Further, a catalytic amount (1–2 drops) of dimethylformanide was added thereto, and the reaction mixture was refluxed for 6 hours. After the soluvent and excessive thionylchloride were distilled off under reduced pressure, the chloride thus obtained was dissloved in 10 ml of dichloromethane.

To the solution was added 0.31 g of thiophenol and then 0.392 ml of triethylamine while ice cooling. After the solution was stirred at room temperature for 2 to 3 hours, the reaction mixture was washed with water and then brine, and dried over anhydrous sodium sulfate. Crude crystals obtained by removing the slovent under reduced pressure was washed with diethylether and/or acetone to obtain 1.2 g the objective compound (Compound No. 95 in Table 3). (Yield: 95.2%)

REFERENCE EXAMPLE

Preparation of Intermediate, 3-(2-Nitro-4-methylsulfonylbenzoyl)bicyclo[3.2.1]-octane-2,4-dione To a solution of 10 g of bicyclo[3.2.1]octane-2,4-dione in 100 ml of dichloromethane was added dropwise 70 ml of a dichloromethane solution having dissolved therein 19.1 g of 2-nitro-4-methylsulfonylbenzoyl chloride while ice cooling.

After completion of the dropwise addition, the reaction mixture was stirred for additional 1 hour while ice cooling, diluted with dichloromethane, washed with water, and dried over anhydrous sodium sulfate.

Under reduced pressure, the solvent was distilled off to dryness to obtain 25.2 g crude crystals of an enol ester.

The enol ester was dissolved in 160 ml of acetonitrile without purification, and 20 ml of triethylamine and 4.3 ml of acetone cyanohydrin were added to the resulting solution. The reaction mixture was stirred at room temperature for one night. After being concentrated under reduced pressure, the reaction mixture was poured into water, extracted with dichloromethane, washed with 10% hydrochloric acid and then with saturated saline, and dried over anhydrous sodium sulfate.

The solvent was distilled off under reduced pressure, and the residue was crystallized from diethyl ether to obtain 19 g of the objective compound, 3-(2-nitro-4 -methylsulfonylbenzoyl) bicyclo[3.2.1]octane-2,4-dione. (Yield: 71.8%)

Tables 3-1 through 3-9 and Table 4 show specific examples of the compounds prepared by the above-described methods. However, the present invention should not be construed as being limited thereto.

TABLE 3-1

| Compound No. | n | R¹ | B, D, E | Properties (mp. °C.) | NMR Data δ (ppm) from TMS in CDCl3, J (Hz) |
|---|---|---|---|---|---|
| 60 | 0 | $C_2H_5-$ | B:$NO_2$ D:H E:$SO_2CH_3$ | 152~155 | 8.5(1H, d, J=2), 8.1(1H, dd, J=8.2), 7.3(1H, d, J=8), 3.1(3H, s), 1.2~3.8(13H, m) |
| 61 | 0 | $C_2H_5-$ | B:$NO_2$ D:H E:Cl | 112~113 | 7.9(1H, d, J=2), 7.5(1H, dd, J=8.2), 7.1(1H, d, J=8), 1.2~3.8(13H, m) |
| 62 | 0 | Ph— | B:$NO_2$ D:H E:$SO_2CH_3$ | Oil | 7.0~8.5(8H, m), 3.1(3H, s), 1.4~3.0(8H, m) |

TABLE 3-2

| Compound No. | n | R¹ | B, D, E | Properties (mp. °C.) | NMR Data δ (ppm) from TMS in CDCl3, J(Hz) |
|---|---|---|---|---|---|
| 63 | 0 | 4-Cl—$PhCH_2$— | B:$NO_2$ D:H E:$SO_2CH_3$ | 195~197 | 7.0~8.4(7H, m), 4.2(2H, s), 3.1(3H, s), 1.4~3.8(m, 8H) |
| 64 | 2 | 4-Cl—$PhCH_2$— | B:$NO_2$ D:H E:$SO_2CH_3$ | 204~205 | 7.2~8.3(7H, m), 5.3(2H, s), 3.2(3H, s), 1.5~3.5(8H, m) |
| 65 | 0 | $PhCH_2$— | B:$NO_2$ D:H E:$SO_2CH_3$ | 192~192.5 | 7.2~8.5(8H, m), 4.25(2H, s), 3.1(3H, s), 1.5~3.8(8H, m) |
| 66 | 0 | 2-$CH_3$—Ph— | B:$NO_2$ D:H E:$SO_2CH_3$ | 171~173 | 7.0~8.6(7H, m), 3.1(3H, s), 2.5(3H, s), 1.5~3.2(8H, m) |
| 67 | 0 | 4-F—Ph— | B:$NO_2$ D:H E:$SO_2CH_3$ | 177~179 | 7.0~8.6(7H, m), 3.1(3H, s), 1.5~3.0(8H, m) |
| 68 | 0 | 2,6-$Cl_2$—Ph | B:$NO_2$ D:H E:$SO_2CH_3$ | 214~216 | 7.1~8.6(6H, m), 3.1(3H, s), 1.4~3.1(8H, m) |

TABLE 3-3

| Compound No. | n | R¹ | B, D, E | Properties (mp. °C.) | NMR Data δ (ppm) from TMS in CDCl3, J(Hz) |
|---|---|---|---|---|---|
| 69 | 0 | 3-Cl—Ph— | B:$NO_2$ D:H E:$SO_2CH_3$ | 93~95 | 7.1~8.5(7H, m), 3.1(3H, s), 1.4~3.2(8H, m) |
| 70 | 0 | 4-$CH_3$—Ph— | B:$NO_2$ D:H E:$SO_2CH_3$ | 146~148 | 7.0~8.6(7H, m), 3.1(3H, s), 2.4(3H, s), 1.5~3.0(8H, m) |
| 71 | 0 | —$CH_2CO_2Me$ | B:$NO_2$ D:H E:$SO_2CH_3$ | 80~90 | 7.2~8.6(3H, m), 3.8(3H, s), 3.75(2H, s), 3.1(3H, s), 1.5~3.0(8H, m) |
| 72 | 0 | 4-F—Ph— | B:$NO_2$ D:$OCH_3$ E:Cl | 165 | 6.7~7.7(6H, m), 3.9(3H, s), 1.5~3.2(8H, m) |
| 73 | 0 | 2,6-$Cl_2$—Ph— | B:$NO_2$ D:$OCH_3$ E:Cl | 170 | 6.9~7.6(5H, m), 3.9(3H, s), 1.4~3.0(8H, m) |
| 74 | 0 | 4-F—Ph— | B:$NO_2$ D:$OC_2H_5$ E:Cl | 154 | 6.8~7.6(6H, m), 4.1(2H, q, J=6), 1.5~3.0(8H, m), 1.3(3H, t, J=6) |

TABLE 3-4

| Compound No. | n | R¹ | B, D, E | Properties (mp. °C.) | NMR Data δ (ppm) from TMS in CDCl3, J(Hz) |
|---|---|---|---|---|---|
| 75 | 0 | 2, 6-Cl$_2$—Ph— | B:NO$_2$<br>D:OC$_2$H$_5$<br>E:Cl | | |
| 76 | 0 | 2, 6-Cl$_2$—Ph— | B:NO$_2$<br>D:H<br>E:SCH$_3$ | 125~135 | 7.1~7.5(6H, m), 2.6(3H, s),<br>1.5~3.0(8H, m) |
| 77 | 0 | 2, 6-Cl$_2$—Ph— | B:Cl<br>D:H<br>E:SO$_2$CH$_3$ | 193~195 | 7.1~7.9(6H, m), 3.0(3H, s),<br>1.3~3.0(8H, m) |
| 78 | 0 | 2, 6-Me$_2$—Ph— | B:NO$_2$<br>D:OC$_2$H$_5$<br>E:Cl | 160~162 | 7.1~7.5(5H, m), 4.1(2H, q, J=7),<br>2.4(6H, s), 1.5~3.0(8H, m),<br>1.3(3H, q, J=7) |
| 79 | 0 | 2, 6-Me$_2$—Ph— | B:Cl<br>D:H<br>E:SO$_2$CH$_3$ | 142~145 | 7.1~8.0(6H, m), 3.1(3H, s),<br>2.5(6H, s), 1.5~3.0(8H, m) |
| 80 | 0 | 2, 6-Me$_2$—Ph— | B:NO$_2$<br>D:OCH$_3$<br>E:Cl | 170~172 | 7.1~7.7(5H, m), 4.0(3H, s),<br>2.4(6H, s), 1.5~3.0(8H, m) |

TABLE 3-5

| Compound No. | n | R¹ | B, D, E | Properties (mp. °C.) | NMR Data δ (ppm) from TMS in CDCl3, J(Hz) |
|---|---|---|---|---|---|
| 81 | 0 | 2, 6-Me$_2$—Ph— | B:NO$_2$<br>D:H<br>E:SCH$_3$ | | |
| 82 | 0 | C$_4$H$_9$-t | B:NO$_2$<br>D:H<br>E:SO$_2$CH$_3$ | 165~168 | 8.5(1H, d, J=2), 8.1(1H, dd, J=8.2), 7.3<br>(1H, d, J=8), 4.0(1H, m), 3.1(3H, s), 2.8<br>(1H, m), 1.5~2.5(6H, m), 1.7(9H, s) |
| 83 | 2 | 2, 6-Cl$_2$—Ph— | B:NO$_2$<br>D:H<br>E:SO$_2$CH$_3$ | | |
| 84 | 0 | 2, 6-Cl$_2$—Ph— | B:NO$_2$<br>D:H<br>E:Cl | 246~247 | |
| 85 | 0 | 2, 6-Me$_2$—Ph— | B:NO$_2$<br>D:H<br>E:Cl | 171~173 | 7.95(1H, d, J=2), 7.1~7.7(5H, m),<br>2.5(6H, s), 1.0~3.1(8H, m) |
| 86 | 0 | C$_4$H$_9$-t | B:NO$_2$<br>D:H<br>E:Cl | 142~145 | 7.9(1H, d, J=2), 7.6(1H, dd, J=8.2), 7.3<br>(1H, d, J=8), 3.8~4.1(1H, m), 2.7~3.0<br>(1H, m), 1.6~2.3(6H, m), 1.6(9H, s) |

TABLE 3-6

| Compound No. | n | R¹ | B, D, E | Properties (mp. °C.) | NMR Data δ (ppm) from TMS in CDCl3, J(Hz) |
|---|---|---|---|---|---|
| 87 | 0 | 2,6-Me$_2$—Ph— | B:NO$_2$<br>D:H<br>E:SO$_2$CH$_3$ | 166~169 | 8.6(1H, d, J=2), 8.2(1H, dd, J=8.2), 7.5<br>(1H, d, J=8), 7.2(3H, br, s), 3.1(3H, s),<br>2.5(6H, br, s), 1.5~3.2(8H, m) |
| 88 | 0 | Ph— | B:NO$_2$<br>D:H<br>E:SCH$_3$ | 160~161 | 7.1~7.9(8H, m), 2.5~3.2(2H, m),<br>2.4(3H, s), 1.1~2.2(6H, m) |
| 89 | 0 | 2-CH$_3$—Ph— | B:NO$_2$<br>D:H<br>E:SCH$_3$ | 180~184 | 7.0~7.9(7H, m), 2.6~3.25(2H, m),<br>2.53(3H, s), 2.5(3H, S),<br>1.1~2.4(6H, m) |
| 90 | 0 | 4-CH$_3$—Ph— | B:NO$_2$<br>D:H<br>E:SCH$_3$ | 157~158 | 7.0~7.85(7H, m), 2.6~3.3(2H, m),<br>2.55(3H, s), 2.4(3H, s),<br>1.1~2.2(6H, m) |
| 91 | 0 | 3-Cl—Ph— | B:NO$_2$<br>D:H<br>E:SCH$_3$ | 131~132 | 7.1~7.9(7H, m), 2.7~3.2(2H, m),<br>2.55(3H, s), 1.0~2.4(6H, m) |
| 92 | 0 | 2,5-Cl$_2$—Ph— | B:NO$_2$<br>D:H<br>E:SCH$_3$ | 142~143 | 7.1~7.9(6H, m), 2.65~3.1(2H, m),<br>2.55(3H, s), 1.0~2.4(6H, m) |

TABLE 3-7

| Compound No. | n | R¹ | B, D, E | Properties (mp. °C.) | NMR Data δ (ppm) from TMS in CDCl3, J(Hz) |
|---|---|---|---|---|---|
| 93 | 0 | 4-F—Ph— | B:NO₂ D:H E:SCH₃ | 172–174 | 6.95–7.9(7H, m), 2.6–3.2(2H, m), 2.55(3H, s), 1.1–2.4(6H, m) |
| 94 | 0 | 2, 5-Cl₂—Ph— | B:NO₂ D:H E:SCH₃ | 232–233 | |
| 95 | 0 | Ph— | B:Cl D:H E:SO₂CH₃ | 184–186 | 7.2–7.9(8H, m), 3.05(3H, s), 1.1–3.0(8H, m) |
| 96 | 0 | 2-CH₃—Ph— | B:Cl D:H E:SO₂CH₃ | 116–118 | 7.1–8.0(7H, m), 3.1(3H, s), 2.5(3H, s), 1.4–3.0(8H, m) |
| 97 | 0 | 4-CH₃—Ph— | B:Cl D:H E:SO₂CH₃ | 152–153 | 7.1–8.0(7H, m), 3.05(3H, s), 2.4(3H, s), 1.2–3.0(8H, m) |
| 98 | 0 | 3-Cl—Ph— | B:Cl D:H E:SO₂CH₃ | 166–168 | 7.1–8.0(7H, m), 3.05(3H, s), 1.3–3.2(8H, m) |

TABLE 3-8

| Compound No. | n | R¹ | B, D, E | Properties (mp. °C.) | NMR Data δ (ppm) from TMS in CDCl3, J(Hz) |
|---|---|---|---|---|---|
| 99 | 0 | 2, 5-Cl₂—Ph— | B:Cl D:H E:SO₂CH₃ | 181–182 | 7.2–8.0(6H, m), 3.05(3H, s), 1.1–3.0(8H, m) |
| 100 | 0 | 4-F-Ph | B:Cl D:H E:SO₂CH₃ | 175–177 | 6.9–7.9(7H, m), 3.05(3H, s), 1.3–3.2(8H, m) |
| 101 | 0 | 2, 6-Cl₂—Ph— | B:NO₂ D:H E:OSO₂CH₃ | 165–166 | |
| 102 | 0 | 2, 6-Cl₂—Ph— | B:NO₂ D:H E:SO₂CHF₂ | 73–76 | 7.2–8.8(6H, m), 6.25(1H, t, J=52), 1.0–3.4(8H, m) |
| 103 | 0 | 2, 6-Me₂—Ph— | B:NO₂ D:H E:OSO₂CH₃ | 117–120 | 7.1–8.0(6H, m), 3.2(3H, s), 2.6–3.1(2H, m), 2.5(3H, s), 1.5–2.3(6H, m) |
| 104 | 0 | 2-(MeSO₂)₂—N—Ph— | B:Cl D:H E:SO₂CH₃ | 132–140 | 7.4–8.0(7H, m), 3.5(3H, s), 3.4(3H, s), 3.1(3H, s), 2.7–3.3(2H, m), 1.2–2.6(6H, m) |

TABLE 3-9

| Compound No. | n | R¹ | B, D, E | Properties (mp. °C.) | NMR Data δ (ppm) from TMS in CDCl3, J(Hz) |
|---|---|---|---|---|---|
| 105 | 0 | 2-(MeSO₂)₂—N—Ph— | B:NO₂ D:H E:SO₂CH₃ | 170–180 | 8.6(1H, d, J=2), 8.1(1H, dd, J=8,2), 7.2–7.9(5H, m), 3.5(3H, s), 3.4(3H, s), 3.1(3H, s), 2.6–3.2(2H, m), 1.3–2.3(6H, m) |
| 106 | 0 | Ph— | B:CH₃ D:COOCH₃ E:SO₂CH₃ | 184–186 | 7.2–7.9(7H, m), 3.95(3H, s), 3.15(3H, s), 2.7–3.3(2H, m), 2.4(3H, s), 1.5–2.4(6H, m) |
| 107 | 0 | シクロヘキシル | B:Cl D:H E:SO₂CH₃ | 134–136 | 7.6–7.9(2H, m), 7.5(1H, d, J=8), 2.7–3.7(3H, m), 3.0(3H, s), 1.1–2.5(16H, m) |
| 108 | 2 | Ph— | B:Cl D:H E:SO₂CH₃ | 211.5–213.5 | 7.1–8.2(8H, m), 3.0(3H, s), 1.4–3.3(8H, m) |
| 109 | 0 | C₂H₅ | B:Cl D:H E:SO₂CH₃ | 128–134 | 7.3–7.9(3H, m), 3.8(1H, m), 3.0(3H, s), 2.7–3.1(3H, m), 1.5–2.2(6H, m), 1.2(3H, t, J=3.8) |
| 110 | 2 | 4-CH₃—Ph— | B:Cl D:H E:SO₂CH₃ | 199.5–201.5 | 7.2–8.2(7H, m), 3.1(3H, s), 2.45(3H, s), 1.4–3.4(8H, m), |

TABLE 4

| Compound No. | $R^2$ | B, D, E | Properties (mp. °C.) | NMR Data δ (ppm) from TMS in CDCl3, J (Hz) |
|---|---|---|---|---|
| 111 | 2, 4, 6-Cl$_3$—Ph— | B:NO$_2$ D:H E:Cl | 151~154 | 8.5(1H, d, J=2), 8.2(1H, dd, J=8.2), 7.6(1H, d, J=8), 7.4(2H, s), 3.1(3H, s), 1.4~3.2(8H, m) |
| 112 | 2, 4, 6-Cl$_3$—Ph— | B:Cl D:H E:SO$_2$CH$_3$ | | 7.2~7.9(5H, m), 3.1(3H, s), 1.5~3.2(8H, m) in DMSO-d6 |
| 113 | 2, 4, 6-Cl$_3$—Ph— | B:NO$_2$ D:H E:SO$_2$CH$_3$ | 214~217 | 8.5(1H, d, J=2), 8.1(1H, dd, J=8.2), 7.55(1H, d, J=8), 7.3(2H, s), 3.1(3H, s), 1.3~3.2(8H, m) |

The compounds of the present invention represented by general formula (I) can be used to control a wide variety of noxious weeds. The compounds of the present invention exhibit selective herbicidal activities with considerably reduced phytotoxicity on paddy rice plant as compared with known dione herbicidal active compounds. The compounds of the present invention have features that they exhibit remarkable herbicidal activities on both annual and perennial weeds growing on paddy field, for example, a barn millet (a popular name for Echinochloa, annual Graminae, representative strong weed on paddy fields), *Monochoria vaginalis Presl.* (annual Pontederiaceae, strong weed on paddy fields), *Cyperus difformis L.* (annual Cyperaceae, strong weed on paddy fields), *Eleocharis acicularis Roem. et Schult. var. longiseta Svenson* (perennial Cyperaceae, grows on swamps, waterways, paddy fields, representative perennial weed), *Sagittaria pygmaea Miq.* (Alismataceae, a perennial weed growing on paddy fields, swamps, ditches), *Scirpus hotarui Ohwi, Cyperus serotinus Rottb.* (perennial weeds belonging to the family Cyperaceae, grow on paddy fields, swamps, ditches), etc., and that they exhibit low phytotoxicities on paddy rice plant.

Since the compounds of the present invention represented by general formula (I) exhibit excellent herbicidal activities on weeds before germination and during growth, they are useful as herbicides for soil treatments before and after transplantation of young seedlings of paddy rice plant as well as herbicides for soil treatments before transplantation of crops, and for treatments of stems and leaves of crops before their transplantation and during their growth.

Generally, herbicidal compositions containing the compounds of the present invention as active ingredients are used after being formulated into suitable forms for application before they can be used actually.

That is, the above-described compounds are blended with suitable inert carriers, if necessary together with auxiliary agents, in appropriate proportions, to allow them to be dissolved, separated, suspended, mixed, impregnated, adsorbed or attached, so that they can be formulated into suitable forms, for example, suspensions, emulsions, solutions, wettable powders, dry flowable, dusts, granules, tablets, etc.

The inert carriers which can be used in the present invention may be either solid or liquid. As materials for solid carriers, there can be used soybean powder, grain powder, wood powder, bark powder, saw dust, tobacco stem powder, walnut nutshell powder, bran, fiber powder, plant powder such as residues after extraction of plant essences; fiber products such as paper, corrugated board, used cloths; synthetic polymers such as pulverized synthetic resins; inorganic mineral powders such as clays (e.g., kaolin, bentonite, acid clay), talcs (talc, pyrophyllite), silicas (e.g., diatomaceous earth, silica sand, mica, white carbon (synthetic highly dispersed silicic acid also called water-containing fine silicium or water-containing silicic acid, some products containing calcium silicate as a main component)), activated carbon, sulfur powder, pumice, calcined diatomaceous earth, ground brick, fly ash, sand, calcium carbonate, calcium phosphate, etc.; chemical fertilizers such as ammonium sulfate, ammonium phosphate, ammonium nitrate, urea., ammonium chloride, potassium chloride, potassium nitrate, compost, etc. These can be used alone or two or more of them can be used in admixture.

Materials for liquid carriers can be selected from those substances which have solvating power by themselves and in addition thereto those substances which can disperse active ingredients with the aid of auxiliary agents although they themselves have no such solvating power. Specific examples thereof include water, alcohols (e.g., methanol, ethanol, isopropanol, butanol, ethylene glycol), ketones (e.g., acetone, methyl ethyl ketone, methyl isobutyl ketone, diisobutyl ketone, cyclohexanone), ethers (e.g., ethyl ether, dioxane, cellosolve, dipropyl ether, tetrahydrofuran), aliphatic hydrocarbons (e.g., gasoline, mineral oil), aromatic hydrocarbons (e.g., benzene, toluene, xylene, solvent naphtha, alkylnaphthalene), halogenated hydrocarbons (e.g., dichloroethane, chlorinated benzene, chloroform, carbon tetrachloride), esters (e.g., ethyl acetate, dibutyl phthalate, diisopropyl phthalate, dioctyl phthalate), acid amides (e.g., dimethylformamide, diethylformamide, dimethylacetamide), nitriles (e.g., acetonitrile), dimethylsulfoxide, etc. These may be used alone or two or more of them may be used in admixture.

The auxiliary agents include the following substances. The auxiliary agents may be used depending on the purpose. In some cases, two or more auxiliary agents are used in combination. In other cases, no auxiliary agent is used.

Surfactants may be used in order to emulsify, disperse, solubilize and/or wet active ingredients. For example, there can be used polyoxyethylene alkyl aryl ether, polyoxyethylene alkyl ether, polyoxyethylene higher fatty acid ester, polyoxyethylene resin acid ester, polyoxyethylene sorbitan monolaurate, polyoxyethylene sorbitan monooleate, alkyl aryl sulfonate, naphthalenesulfonate condensation product, ligninsulfonate, higher alcohol sulfate, etc. For the purpose of dispersion stabilization, adhesion and/or binding, there may be used advantageously casein, gelatin, starch, alginic acid, methyl cellulose, carboxymethylcellulose, gum arabic, polyvinyl alcohol, pine root oil, sugar cane oil, bentonite, ligninsulfonate, etc.

In order to improve flowability of solid products, there may be used, for example, waxes, stearates, alkyl phosphates, etc.

As deflocculating agent for suspension products, there may be used, for example, naphthalenesulfonic acid condensation products, condensed phosphoric acid, etc.

It is possible to add a defoaming agent such as silicone oil.

Amounts of the active ingredients in a formulation may be adjusted, if desired. In the case of dusts or granules, the amount of the active ingredient is usually 0.2 to 20% by weight, while in the case of emulsions and wettable powders, it is usually 0.1 to 50% by weight.

EXAMPLES

The followings are typical examples of formulations according to the present invention. Needless to say, the content of the active ingredient may be changed within the above-described range. All "parts" in the following are by weight.

Example 1

Wettable Powder a compound in Table 2 (50 parts), 20 parts of diatomaceous earth, 22 parts of clay, 3 parts of white carbon, 2 parts of sodium ligninsulfonate and 3 parts of sodium alkylnaphthalenesulfonate were mixed and ground to obtain a wettable powder containing 50% of an active ingredient.

Example 2

Granule

A compound in Table 2 (0.35 part), 25 parts of bentonite, 70.65 parts of talc and 2 parts of sodium dodecylbenzenesulfonate were mixed. The mixture was kneaded together with about 20 parts of water in a kneader, and then granulated using a granulator, followed by drying and grain dressing to obtain granules containing 0.35% of active ingredient.

The herbicides of the present invention can be used by applying as they are or after being suitably diluted or suspended with water or the like in phytotoxically or growth control effective amounts on weeds or stems and leaves of weeds or in soil if growth or germination, respectively, of the weeds are undesirable.

The doses of the herbicides of the present invention may vary depending on various factors, for example, purposes, kinds of weeds to be killed or controlled, states of germination or growth of weeds or crops, tendency of germination of weeds, weather, formulations, method of application, place of application, time of application, etc.

In the case where the herbicides of the present invention are used as a selective herbicide for paddy rice plant, for example, it is sufficient to use 5 to 1,000 g/ha, preferably 10 to 500 g/ha, of the compound of the present invention.

In the case where the herbicide of the present invention is used as a mixture with one or more other herbicides, it is possible to use the compound of the present invention in doses lower than that described above since it will be effective at a lower dose than its dose when it is used alone.

Although the herbicides of the present invention are valuable as herbicides particularly for weeds for paddy rice plant before their germination and during growth, it is possible to use them as mixtures with other herbicides to widen weeds spectrum and optimal time for prevention or reduce the doses without departing from the scope of the present invention.

EFFECT OF THE INVENTION

The herbicides of the present invention can generally prevent a wide variety of noxious weeds, and more particularly, exhibit considerably reduced phytotoxicity on paddy rice plant and can prevent weeds on paddy field selectively.

TEST EXAMPLES

Hereinafter, the present invention will be illustrated in detail wit reference to test examples below. However, the present invention should not be construed as being limited thereto.

Test Example 5

Granule Test

A 1/5,000 are Wager pot was filled with paddy field soil and plowed. The depth of water was set to 4 cm. Seeds of *Echinochloa crus-galli* P. Beauv., *Monochoria vaginalis* Presl., *Ammannia multiflora* Roxb., and *Scirpus hotarui* were sown and bulbs of *Sagittaria trifolia* L., *Sagittaria pygmaea* Miq., *Cyperus serotinus* Rottb., and *Eleocharis kuroguwai* Ohwi were planted. Then, two-leaf rice plant (variety: Koshihikari) was transplanted in a population of 6 individuals per pot (at a depth of 1 cm: 3 individuals, 3 cm: 3 individuals). On day 10 after transplantation, granules of the compounds of the present invention, i.e., Compounds Nos. 63, 65, 66, 68, 70, 88, 89, 90, 91, 93, 95, 96, 97, 98, 100 and 104, prepared according to Example 2, and granules prepared from Compound (A) disclosed in Japanese Patent Application Laid-open No. 152642/1986, Compound (B) disclosed in Japanese Patent Application Laid-open No. 292755/1987 and Compound (C) disclosed in Japanese Patent Application Laid-open No. 6425/1990 were applied on the surface of the water.

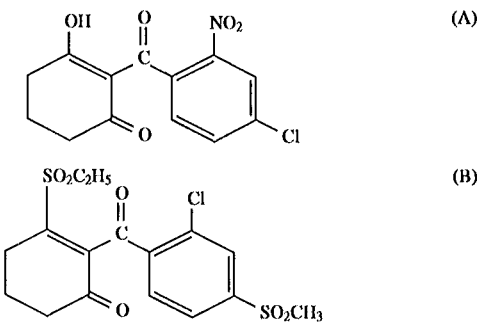

-continued

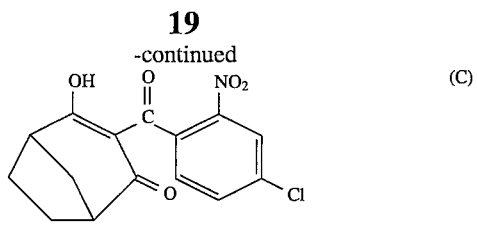

(C)

On the next day and the next day but one after the treatment, water leakage operations were conducted at a rate of 3 cm/day. On day 21 from the treatment, observation and evaluation were made according to the following criteria. Results are shown in Tables 5-1 and 5-2.

0: No effect, no phytotoxicity
10: completely killed

Test Example 2

Wettable Powder Test

A 325 cm$^2$ flower pot was filled with farm soil, and seeds of various weeds, i.e., *Digitaria adscendens Henr. Echinochloa crus-galli P. Beauv., Setaria viridis P. Beauv., Polygonum blumei Meisn., Chenopodium album L., Abutilon theophrast MEDIK., Ambrosia artemisiaefolia L. var. elator Desc., Amaranthus retroflexus L., Xanthium strumarium L., Pharbitis purpurea Voigt.*, and seeds of various crops, i.e., soybean, maize, wheat, cotton plant and sugar beet, were sown therein. Pre-emergence soil treatment was conducted on day 1 after the sowing, foliage treatment was conducted day 10 after the sowing with the compounds of the present invention, i.e., Compounds Nos. 62, 64, 67, 68, 71, 90, 91, 93, 95, 97, 100 and 104, and an aqueous solution of the above-described comparative compound A (wettable powder) were applied by spraying. On day 21 after the treatment, observation and evaluation were made according to the following criteria. Results are shown in Table 6.

0: No effect, no phytotoxicity
10: completely killed

TABLE 5-1

Herbicidal Effect and Phytotoxicity on Rice Plant

| Compound No. | Dose (g/ha) | RICE 1 cm | RICE 3 cm | ECCGP. | SCHO. | CYSR. | ELKO. | MOVP. | AMMR. | SAPM. | SATL. |
|---|---|---|---|---|---|---|---|---|---|---|---|
| 63 | 1000 | 0.0 | 0.0 | 8.5 | 9.0 | 9.5 | 10.0 | 9.0 | 9.0 | 8.5 | — |
|    | 500  | 0.0 | 0.0 | 7.5 | 8.5 | 9.0 | 9.5 | 9.0 | 9.0 | 7.0 | — |
| 65 | 1000 | 0.5 | 0.0 | 10.0 | 9.0 | 10.0 | 10.0 | 9.5 | 9.5 | 10.0 | — |
|    | 500  | 0.0 | 0.0 | 10.0 | 9.0 | 9.5 | 10.0 | 9.5 | 9.0 | 9.0 | — |
| 66 | 1000 | 1.5 | 0.5 | 10.0 | 9.0 | 10.0 | 10.0 | 9.5 | 9.5 | 9.5 | — |
|    | 500  | 0.0 | 0.0 | 10.0 | 9.0 | 10.0 | 10.0 | 9.5 | 9.5 | 9.5 | — |
| 68 | 1000 | 0.0 | 0.0 | 10.0 | 9.0 | 9.5 | 10.0 | 10.0 | 9.5 | 10.0 | — |
|    | 500  | 0.0 | 0.0 | 10.0 | 9.0 | 8.5 | 9.5 | 9.5 | 9.5 | 9.5 | — |
| 70 | 1000 | 2.0 | 0.0 | 10.0 | 9.5 | 10.0 | 10.0 | 10.0 | 9.0 | 10.0 | — |
|    | 500  | 0.5 | 0.0 | 10.0 | 9.5 | 10.0 | 10.0 | 10.0 | 9.0 | 10.0 | — |
| 88 | 1000 | 2.5 | 1.5 | 10.0 | 9.0 | 10.0 | 10.0 | 9.8 | 9.5 | 10.0 | 9.5 |
|    | 500  | 0.5 | 0.0 | 9.5 | 9.0 | 10.0 | 10.0 | 9.5 | 9.0 | 9.8 | 9.5 |
| 89 | 1000 | 0.0 | 0.0 | 10.0 | 9.0 | 9.8 | 9.5 | 9.5 | 9.0 | 10.0 | 10.0 |
|    | 500  | 0.0 | 0.0 | 9.5 | 9.0 | 9.5 | 9.0 | 9.0 | 9.0 | 9.5 | 9.5 |
| 90 | 1000 | 3.5 | 2.5 | 10.0 | 9.5 | 10.0 | 9.8 | 9.5 | 9.5 | 10.0 | 10.0 |
|    | 500  | 2.0 | 0.0 | 10.0 | 9.5 | 9.8 | 9.5 | 9.0 | 9.0 | 9.5 | 9.5 |
| 91 | 1000 | 1.5 | 0.0 | 10.0 | 9.0 | 9.8 | 9.8 | 9.5 | 9.0 | 9.5 | 9.0 |
|    | 500  | 0.0 | 0.0 | 9.5 | 8.5 | 9.5 | 9.0 | 9.0 | 9.0 | 9.0 | 8.5 |
| 93 | 1000 | 3.5 | 2.0 | 10.0 | 9.0 | 10.0 | 9.8 | 9.8 | 9.5 | 10.0 | 9.5 |
|    | 500  | 2.0 | 0.0 | 9.5 | 9.0 | 9.8 | 9.5 | 9.5 | 9.0 | 9.8 | 9.5 |

TABLE 5-2

Herbicidal Effect and Phytotoxicity on Rice Plant

| Compound No. | Dose (g/ha) | RICE 1 cm | 3 cm | ECCGP. | SCHO. | CYSR. | ELKO. | MOVP. | AMMR. | SAPM. | SATL. |
|---|---|---|---|---|---|---|---|---|---|---|---|
| 95 | 1000 | 0.0 | 0.0 | 10.0 | 9.5 | 10.0 | 10.0 | 10.0 | 9.5 | 9.8 | 9.5 |
|  | 500 | 0.0 | 0.0 | 10.0 | 9.5 | 10.0 | 10.0 | 9.8 | 9.0 | 9.0 | 9.0 |
| 96 | 1000 | 3.5 | 2.5 | 10.0 | 9.5 | 10.0 | 9.5 | 9.8 | 9.0 | 10.0 | 9.5 |
|  | 500 | 2.0 | 0.0 | 10.0 | 9.5 | 9.8 | 9.5 | 9.0 | 9.0 | 9.5 | 9.0 |
| 97 | 1000 | 0.0 | 0.0 | 10.0 | 10.0 | 10.0 | 10.0 | 10.0 | 9.5 | 10.0 | 10.0 |
|  | 500 | 0.0 | 0.0 | 10.0 | 9.5 | 10.0 | 10.0 | 10.0 | 9.0 | 9.5 | 9.5 |
| 98 | 1000 | 0.0 | 0.0 | 10.0 | 9.5 | 10.0 | 10.0 | 10.0 | 9.0 | 9.5 | 9.5 |
|  | 500 | 0.0 | 0.0 | 10.0 | 9.5 | 9.8 | 9.5 | 9.5 | 9.0 | 9.0 | 9.0 |
| 100 | 1000 | 3.5 | 2.5 | 10.0 | 9.5 | 10.0 | 10.0 | 10.0 | 9.5 | 10.0 | 9.8 |
|  | 500 | 2.0 | 0.0 | 10.0 | 9.5 | 10.0 | 10.0 | 9.8 | 9.0 | 9.8 | 9.5 |
| 104 | 1000 | 2.5 | 1.5 | 10.0 | 9.5 | 10.0 | 10.0 | 9.8 | 9.5 | 10.0 | 9.5 |
|  | 500 | 0.5 | 0.0 | 10.0 | 9.5 | 10.0 | 9.8 | 9.5 | 9.0 | 9.8 | 9.5 |
| Compara. Compound A | 000 | 10.0 | 10.0 | 10.0 | 10.0 | 9.8 | 10.0 | 10.0 | 9.5 | 9.5 | 10.0 |
|  | 500 | 10.0 | 9.5 | 10.0 | 10.0 | 9.8 | 10.0 | 10.0 | 9.0 | 9.5 | 10.0 |
| Compara. Compound B | 1000 | 9.5 | 9.0 | 10.0 | 9.8 | 9.5 | 8.0 | 10.0 | 9.5 | 10.0 | - - |
|  | 500 | 9.5 | 8.5 | 9.5 | 9.5 | 8.5 | 6.5 | 9.5 | 9.5 | 9.8 | - - |
| Compara. Compound C | 1000 | 10.0 | 10.0 | 10.0 | 10.0 | 10.0 | 10.0 | 10.0 | 9.8 | 9.8 | - - |
|  | 500 | 10.0 | 10.0 | 10.0 | 9.8 | 9.8 | 9.8 | 9.5 | 9.5 | 9.5 | - - |

TABLE 6-1

Herbicidal Effect and Phytotoxicity

| Compound No. | Dose (g/ha) | Phytotoxicity | | | | | Herbicidal Effect | | | |
|---|---|---|---|---|---|---|---|---|---|---|
| | | MAIZE | SOYBEAN | WHEAT | BEET | COTTON | DIAIL | ECCGP. | SEVP. B. | POBME. |
| Compara. Compound A | 1000 | 9.5 | 9.0 | 9.5 | 10.0 | 10.0 | 10.0 | 10.0 | 9.5 | 10.0 |
|  | 500 | 8.0 | 7.5 | 8.5 | 9.5 | 10.0 | 9.5 | 9.0 | 8.0 | 9.5 |
|  | 250 | 6.5 | 5.0 | 6.0 | 8.0 | 9.0 | 9.0 | 9.0 | 8.0 | 9.0 |
| 62 | 1000 | 3.5 | 4.0 | 2.0 | 4.0 | 4.5 | 10.0 | 10.0 | 10.0 | 10.0 |
|  | 500 | 0.0 | 1.5 | 0.0 | 1.5 | 1.5 | 10.0 | 10.0 | 9.5 | 10.0 |
|  | 250 | 0.0 | 0.0 | 0.0 | 0.0 | 0.0 | 9.5 | 9.0 | 8.5 | 9.5 |
| 64 | 1000 | 3.0 | 3.5 | 1.5 | 2.5 | 2.5 | 9.5 | 10.0 | 9.5 | 10.0 |
|  | 500 | 0.0 | 1.0 | 0.0 | 1.0 | 2.0 | 9.0 | 9.5 | 9.0 | 10.0 |
|  | 250 | 0.0 | 0.0 | 0.0 | 0.0 | 0.0 | 8.5 | 8.0 | 8.0 | 9.0 |
| 67 | 1000 | 3.5 | 4.5 | 2.0 | 3.0 | 3.0 | 10.0 | 10.0 | 9.5 | 10.0 |
|  | 500 | 1.0 | 1.5 | 0.0 | 1.5 | 1.5 | 9.5 | 9.0 | 9.0 | 9.5 |
|  | 250 | 0.0 | 0.0 | 0.0 | 0.0 | 0.0 | 9.0 | 9.0 | 8.5 | 9.0 |
| 68 | 1000 | 2.5 | 2.0 | 1.5 | 2.0 | 2.0 | 9.5 | 9.5 | 9.5 | 10.0 |
|  | 500 | 0.0 | 0.0 | 0.0 | 0.0 | 1.5 | 9.0 | 9.0 | 9.0 | 9.5 |
|  | 250 | 0.0 | 0.0 | 0.0 | 0.0 | 0.0 | 8.0 | 8.5 | 9.0 | 9.0 |
| 71 | 1000 | 3.0 | 2.5 | 2.0 | 3.0 | 3.0 | 10.0 | 10.0 | 9.5 | 10.0 |
|  | 500 | 0.0 | 0.0 | 0.0 | 1.5 | 2.0 | 9.5 | 9.0 | 9.0 | 10.0 |
|  | 250 | 0.0 | 0.0 | 0.0 | 0.0 | 0.0 | 8.5 | 8.0 | 8.0 | 9.0 |

| Compound No. | Herbicidal Effect | | | | | |
|---|---|---|---|---|---|---|
| | CHAL. | AMAL. | AMRL. | XASL. | ABTM. | PHPVO. |
| Compara-Compound A | 10.0 | 9.5 | 10.0 | 9.5 | 10.0 | 9.5 |
|  | 9.0 | 9.0 | 10.0 | 9.0 | 9.5 | 9.0 |
|  | 8.5 | 8.0 | 9.5 | 8.0 | 9.0 | 8.0 |
| 62 | 10.0 | 10.0 | 10.0 | 10.0 | 10.0 | 10.0 |
|  | 10.0 | 9.5 | 10.0 | 9.5 | 10.0 | 9.5 |
|  | 9.5 | 9.0 | 9.5 | 9.0 | 9.5 | 9.0 |
| 64 | 10.0 | 10.0 | 10.0 | 9.5 | 10.0 | 9.5 |
|  | 9.0 | 9.0 | 9.5 | 9.0 | 10.0 | 9.0 |
|  | 9.0 | 8.5 | 9.5 | 9.0 | 9.0 | 8.5 |
| 67 | 10.0 | 10.0 | 10.0 | 9.5 | 10.0 | 10.0 |
|  | 9.0 | 9.5 | 9.5 | 9.0 | 9.5 | 9.5 |
|  | 8.5 | 9.0 | 9.0 | 8.5 | 9.0 | 8.5 |
| 68 | 10.0 | 10.0 | 10.0 | 9.5 | 10.0 | 9.5 |
|  | 9.5 | 9.0 | 9.5 | 9.0 | 9.5 | 9.0 |
|  | 8.5 | 9.0 | 9.0 | 9.0 | 9.0 | 9.0 |
| 71 | 10.0 | 10.0 | 10.0 | 10.0 | 10.0 | 10.0 |
|  | 9.0 | 9.0 | 9.5 | 9.5 | 10.0 | 9.5 |
|  | 9.0 | 8.5 | 9.0 | 9.0 | 9.5 | 9.0 |

TABLE 6-2

| | | Herbicidal Effect and Phytotoxicity | | | | | | | | |
|---|---|---|---|---|---|---|---|---|---|---|
| Compound No. | Dose (g/ha) | Phytotoxicity | | | | | Herbicidal Effect | | | |
| | | MAIZE | SOYBEAN | WHEAT | BEET | COTTON | DIAH. | ECCGP. | SEVP. B. | POBME. |
| 90 | 1000 | 2.5 | 3.5 | 3.0 | 4.5 | 3.5 | 10.0 | 9.5 | 9.5 | 10.0 |
| | 500 | 1.0 | 2.0 | 1.5 | 2.0 | 1.5 | 9.5 | 9.0 | 9.0 | 10.0 |
| | 250 | 0.0 | 0.5 | 0.0 | 0.5 | 0.0 | 9.0 | 9.0 | 8.5 | 9.5 |
| 91 | 1000 | 2.0 | 2.5 | 1.5 | 3.0 | 2.5 | 10.0 | 9.5 | 9.5 | 10.0 |
| | 500 | 0.0 | 1.5 | 0.0 | 2.0 | 0.0 | 9.0 | 8.5 | 9.0 | 9.5 |
| | 250 | 0.0 | 0.0 | 0.0 | 0.0 | 0.0 | 8.5 | 8.0 | 8.0 | 9.0 |
| 93 | 1000 | 2.5 | 4.5 | 2.5 | 3.5 | 3.0 | 9.5 | 9.5 | 9.0 | 9.5 |
| | 500 | 1.0 | 2.0 | 1.0 | 2.0 | 1.5 | 9.0 | 9.0 | 9.0 | 9.0 |
| | 250 | 0.0 | 0.5 | 0.0 | 1.0 | 0.0 | 9.0 | 8.5 | 8.5 | 9.0 |
| 95 | 1000 | 0.0 | 1.5 | 0.0 | 3.0 | 2.0 | 9.5 | 9.5 | 9.0 | 10.0 |
| | 500 | 0.0 | 0.0 | 0.0 | 0.0 | 0.0 | 9.0 | 9.0 | 9.0 | 9.0 |
| | 250 | 0.0 | 0.0 | 0.0 | 0.0 | 0.0 | 9.0 | 8.5 | 8.5 | 9.0 |
| 97 | 1000 | 0.0 | 2.5 | 2.0 | 3.0 | 2.5 | 10.0 | 10.0 | 9.5 | 10.0 |
| | 500 | 0.0 | 0.0 | 0.0 | 0.0 | 0.0 | 10.0 | 9.5 | 9.0 | 10.0 |
| | 250 | 0.0 | 0.0 | 0.0 | 0.0 | 0.0 | 9.0 | 9.0 | 9.0 | 9.0 |
| 100 | 1000 | 2.5 | 3.0 | 2.0 | 2.5 | 2.5 | 10.0 | 9.5 | 9.5 | 10.0 |
| | 500 | 0.5 | 1.5 | 1.0 | 0.5 | 0.0 | 9.5 | 9.0 | 9.0 | 10.0 |
| | 250 | 0.0 | 0.0 | 0.0 | 0.0 | 0.0 | 9.0 | 9.0 | 8.5 | 9.5 |
| 104 | 1000 | 2.5 | 3.0 | 2.0 | 3.0 | 2.5 | 10.0 | 9.5 | 9.5 | 10.0 |
| | 500 | 0.5 | 2.0 | 1.5 | 2.5 | 0.0 | 9.5 | 9.0 | 9.0 | 10.0 |
| | 250 | 0.0 | 0.0 | 0.0 | 0.0 | 0.0 | 9.0 | 8.5 | 9.0 | 9.5 |

| Compound No. | Herbicidal Effect | | | | | |
|---|---|---|---|---|---|---|
| | CHAL. | AMAL. | AMRL. | XASL. | ABTM. | PHPVO. |
| 90 | 10.0 | 10.0 | 10.0 | 10.0 | 10.0 | 10.0 |
| | 10.0 | 9.5 | 10.0 | 9.5 | 10.0 | 9.5 |
| | 9.5 | 9.5 | 9.5 | 9.0 | 9.5 | 9.5 |
| 91 | 9.5 | 10.0 | 10.0 | 9.5 | 10.0 | 9.5 |
| | 9.5 | 9.5 | 9.5 | 9.0 | 9.5 | 9.0 |
| | 9.0 | 9.0 | 9.5 | 9.0 | 9.0 | 9.0 |
| 93 | 10.0 | 10.0 | 10.0 | 9.5 | 10.0 | 9.5 |
| | 9.5 | 9.5 | 9.5 | 9.0 | 9.5 | 9.5 |
| | 9.0 | 8.5 | 9.0 | 9.0 | 9.0 | 9.0 |
| 95 | 10.0 | 9.5 | 10.0 | 9.5 | 10.0 | 9.5 |
| | 9.5 | 9.0 | 9.0 | 9.0 | 9.5 | 9.0 |
| | 9.0 | 9.0 | 9.0 | 8.5 | 9.0 | 9.0 |
| 97 | 10.0 | 10.0 | 10.0 | 10.0 | 1.0 | 10.0 |
| | 9.5 | 9.5 | 10.0 | 9.5 | 10.0 | 9.5 |
| | 9.5 | 9.0 | 9.5 | 9.0 | 9.5 | 9.0 |
| 100 | 10.0 | 10.0 | 10.0 | 10.0 | 10.0 | 10.0 |
| | 10.0 | 9.5 | 10.0 | 9.5 | 1.0 | 9.5 |
| | 9.5 | 9.5 | 9.5 | 9.5 | 9.5 | 9.0 |
| 104 | 10.0 | 10.0 | 10.0 | 9.5 | 10.0 | 10.0 |
| | 9.5 | 9.5 | 10.0 | 9.0 | 1.0 | 9.5 |
| | 9.5 | 9.0 | 9.5 | 9.0 | 9.5 | 9.0 |

Abbreviation

ECCP.: *Echinichloa crus-galli P.Beauv.*
SCHO.: *Scirpus hotarui Ohwi.*
CYSR.: *Cyperus serotinus Rottb.*
ELKO.: *Eleocharis kuroguwai Ohwi*
MOVP. *Monochoria vaginalis Presl.*
AMMR.: *Ammannia multiflora Roxb.*
SAPM.: *Sagittaria pygmaea Miq.*
SATL.: *Sagittaria triflolia L.*
DIAH.: *Digitaria adscendens Henr.*
SEVP.B.: *Setaria viridis P.Beauv.*
POBME.: *Polygonum blumei Meisn.*
CHAL.: *Chenopodium album L.*
AMAL.: *Ambrosia artemisiaefolia L. var. elator Desc.*
AMRL.: *Amaranthus retroflexus L.*
XASL.: *Xanthium strumarium L.*
ABTM.: *Abutilon theophrasti MEDIK*
PHPVO.: *Pharbitis purpurea Voigt.*

What is claimed is:

1. A substituted benzoyl cyclic enone derivative represented by general formula (I)

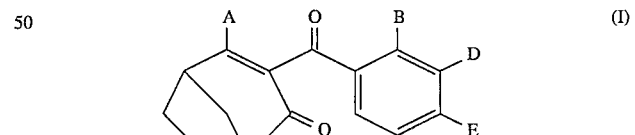

wherein A represents a —S(O)nR$^1$ group in which n is 0 or 2 and R$^1$ represents
 a lower alkyl group having 1–4 carbon atoms which may be substituted with a lower alkoxycarbonyl group having 2–3 carbon atoms;
 a cycloalkyl group having 3–6 carbon atoms;
 a benzyl group which may be substituted with 1 to 3 of halogen atoms, methyl groups and/or nitro groups;
 a phenyl group which may be substituted with 1 to 5 halogen atoms, 1 to 3 lower alkyl groups having 1–4 carbon atoms, a lower alkoxy groups having 1–4 carbon atoms, a halomethyl group, a nitro group, a cyano group and/or an amino group substituted with one or two alkyl or alkylsulfonyl groups having 1-2 carbon atoms; or a —OR² group in which R² represents a phenyl group which may be substituted with 1 to 5 halogen atoms and/or 1 to 3 lower alkyl groups having 1–3 carbon atoms;

B represents a halogen atom, a nitro group, a lower alkyl group having 1–2 carbon atoms, or a lower alkylsulfonyl group having 1–2 carbon atoms;

D represents a hydrogen atom, a lower alkyl group having 1–2 carbon atoms, a lower alkoxy group having 1–4 carbon atoms, a lower alkoxymethyl group having 2–4 carbon atoms, or a lower alkoxycarbonyl group having 2–5 carbon atoms;

E represents a halogen atom, a lower alkoxy group having 1–3 carbon atoms which may be substituted with 1 to 3 fluorine atoms, a lower alkylthio group having 1–3 carbon atoms, a lower alkylsulfonyl group having 1–3 carbon atoms which may be substituted with 1 to 3 fluorine atoms, or a lower alkylsulfonyloxy group having 1-3 carbon atoms.

2. A substituted benzoyl cyclic enone derivative represented by general formula (II)

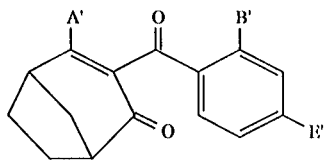

wherein

A' represents a group —S—(O)nR³ in which n is 0 or 2 and R³ represents a phenyl group which may be substituted with 1 to 5 halogen atoms or 1 to 3 lower alkyl groups having 1-4 carbon atoms;

B' represents a halogen atom or a nitro group; and

E' represents a halogen atom, or a lower alkylsulfonyl group having 1–3 carbon atoms which may be substituted with 1 to 3 fluorine atoms.

3. 3-(2-Chloro-4-methylsulfonylbenzoyl)-4-phenylthiobicyclo[3.2.1]oct-3-en-2-one according to claim 1.

4. 3-(2-Chloro-4-methylsulfonylbenzoyl)-4-(4-methylphenylthio)-bicyclo[3.2.1]oct-3-en-2-one according to claim 1.

5. 3-(2-Chloro-4-methylsulfonylbenzoyl)-4-phenylsulfonylbicyclo[3.2.1]oct-3-en-2-one-according to claim 1.

6. 3-(2-Chloro-4-methylsulfonylbenzoyl)-4-(2,6-dimethylphenylthio)-bicyclo[3.2.1]oct-3-en-2-one according to claim 1.

7. 3-(2-Chloro-4-methylsulfonylbenzoyl)-4-(3-chlorophenylthio)-bicyclo[3.2.1]oct-3-en-2-one according to claim 1.

8. 3-(2-Nitro-4-methylsulfonylbenzoyl)-4-(2,6-dichlorophenylthio)-bicyclo[3.2.1]oct-3-en-2-one according to claim 1.

9. A herbicidal composition comprising substituted benzoyl cyclic enone derivative represented by general formula (I) as claimed in claim 1 and an agriculturally acceptable carrier.

10. A method of controlling the growth of undesirable plants on paddy field, comprising the step of applying a herbicidally effective amount of a substituted benzoyl cyclic enone derivative represented by general formula (I) as claimed in claim 1.

* * * * *